United States Patent
Angel et al.

(10) Patent No.: US 6,509,503 B1
(45) Date of Patent: Jan. 21, 2003

(54) PROCESS FOR PREPARING PESTICIDAL INTERMEDIATES

(75) Inventors: Jean-Erick Angel, Saint-Genis-Laval (FR); Gilles Perrin-Janet, Chaponnay (FR); Pierre Leroy, Lyons (FR)

(73) Assignee: Aventis Cropscience S.A. (FR)

( * ) Notice: Subject to any disclaimer, the term of this patent is extended or adjusted under 35 U.S.C. 154(b) by 0 days.

(21) Appl. No.: 10/030,324

(22) PCT Filed: May 11, 2000

(86) PCT No.: PCT/EP00/04595

§ 371 (c)(1),
(2), (4) Date: May 3, 2002

(87) PCT Pub. No.: WO01/69805

PCT Pub. Date: Nov. 23, 2000

(30) Foreign Application Priority Data

May 13, 1999 (GB) .............................................. 9911180

(51) Int. Cl.[7] ............................................. C07C 211/00
(52) U.S. Cl. ........................ 564/442; 564/314; 564/416
(58) Field of Search ................................ 564/314, 416, 564/442

(56) References Cited

U.S. PATENT DOCUMENTS 3,903,090 A 9/1975 Katsutoshi et al.
4,508,922 A 4/1985 Rattan ........................ 564/407

FOREIGN PATENT DOCUMENTS

| DE | 2906574 | 9/1979 |
| JP | 05194330 | 8/1993 |
| JP | 60048500 | 2/1994 |

OTHER PUBLICATIONS

Georg Thieme Verlag, "Methoden der Organischen Chemie (Houben–Weyl) Band E16d" Stuttgart–New York, pp. 985–986.

Georg Thieme Verlag, "Methoden der Organischen Chemie (Houben–Weyl) Band E16a" 1990, Stuttgart–New York pp. 648–653.

J.H. Wotiz, et al., "Low Temperature Animation of Aromatic Polyhalides" Journal of Organic Chemistry, vol. 24, 1959, pp. 595–598.

Nagarajan, K. et al., "Antiimplantation Agents: I–1–Arylthiosemicarbazides" Indian Journal of Chemistry, vol. 23b, No. 12, 1984, pp. 1243–1257.

International Search Report for Intl. Application No. PCT/EP00/04595, mailed Oct. 17, 2000.

*Primary Examiner*—Samuel Barts
(74) *Attorney, Agent, or Firm*—Ostrolenk, Faber, Gerb & Soffen, LLP

(57) ABSTRACT

The invention relates to processes for the preparation of compounds of formula (I) wherein $R^1$ and $R^2$ each independently represent a halogen atom.

7 Claims, No Drawings

PROCESS FOR PREPARING PESTICIDAL INTERMEDIATES

This invention relates to novel processes for preparing intermediates (particularly certain aniline compounds and phenylhydrazine derivatives) useful in the preparation of pesticides.

3,5-Dihaloanilines and particularly 3,5-dichloroaniline are important synthetic intermediates for a number of valuable compounds including agrochemical fungicides for example as described in U.S. Pat. Nos. 3,755,350 and 3,903,090, or German Patent Publication No. 2906574.

Various methods for preparing these compounds (particularly 3,5-dichloroaniline) are known, for example as described in Japanese patent publication numbers 05194330 and 60048500, and U.S. Pat. No. 4,508,922. However these procedures are generally inefficient, slow and suffer from poor selectivity and low yields. Furthermore they generally require the use of ammonia at high temperatures and/or pressures. There remains a need to develop new methods for obtaining these compounds particularly to find procedures which are safe to operate, efficient and can be performed at moderate temperatures and pressures.

The present applicants have surprisingly discovered novel processes for the preparation of certain substituted anilines and phenylhydrazines which do not suffer from these disadvantages, thus providing a new method for preparing valuable synthetic intermediates.

The present invention accordingly provides a process (A) for the preparation of a substituted aniline of formula (I):

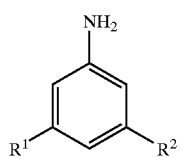

(I)

wherein $R^1$ and $R^2$ each independently represent a halogen atom; or an acid addition salt thereof; which process comprises the hydrogenolysis of a substituted phenylhydrazine of formula (II):

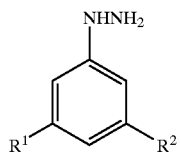

(II)

wherein $R^1$ and $R^2$ are as hereinbefore defined, or an acid addition salt thereof, in the presence of a metal or metal compound (for example a metal salt) under reducing conditions.

Unless otherwise specified in the present specification halogen atoms are selected from fluorine, chlorine, bromine and iodine.

The acid addition salts referred to in the invention are preferably the salts formed from strong acids such as mineral acids, for example sulphuric acid or hydrochloric acid.

The hydrogenolysis may be performed using a metal or metal salt selected from Raney nickel (a nickel-aluminium alloy) optionally in the presence of iron, manganese, cobalt, copper, zinc or chromium; stannous chloride; zinc in the presence of acetic acid; and a molybdenum (III) salt. The reaction may also be carried out using Raney nickel, platinum or palladium (which may be supported on charcoal or other inert material) in the presence of hydrogen gas. When the reaction is performed with hydrogen gas a pressure of 2 to 20 bars (preferably 5 to 10 bars) is generally used. The hydrogenolysis is preferably performed using Raney nickel.

The reaction may be performed in the absence or presence of a solvent, but is generally conducted in a solvent which may be selected from alcohols such as methanol, ethanol, propanol, isopropanol, butanol, isobutanol or tertiary butanol; ethers; aromatic hydrocarbons and water (or mixtures thereof). Methanol and ethanol are preferred solvents.

The reaction temperature is generally from 20° C. to 150° C., preferably from 20° C. to 90° C. The amount of catalyst employed is generally from 0.01 to 3 molar equivalents (preferably from 0.05 to 2 molar equivalents), although when the reaction is carried out under an atmosphere of hydrogen, a smaller amount generally gives satisfactory results.

Process (A) seeks to enable substituted aniline compounds of formula (I) and their acid addition salts thereof to be obtained in high yield from readily available starting materials. Furthermore the reaction can be very simple and economical to perform, and product isolation can be straightforward. Another advantage of this method is that these compounds of formula (I) may be prepared at moderate temperatures and pressures, whereas prior art methods require high temperatures and pressures.

According to a further feature of the present invention there is provided a process (B) for the preparation of a substituted phenylhydrazine of formula (II) as defined above, or an acid addition salt thereof, which comprises the reaction of a compound of formula (III):

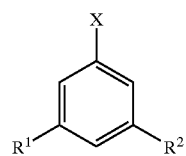

(III)

wherein $R^1$ and $R^2$ are as hereinbefore defined and X represents a halogen atom, with hydrazine or an acid addition salt or source thereof.

By appropriate selection of the halogen atoms which represent $R^1$, $R^2$ and X in formula (III) so that the group X is more reactive than $R^1$ and $R^2$, it is possible to obtain substituted phenylhydrazines of formula (II) and salts thereof having the various combinations of halogen atoms. Particularly preferred compounds are those wherein $R^1$ and $R^2$ in formulae (I) and (II) each represent a chlorine atom.

Compounds of formula (III) are generally known.

Preferably hydrazine hydrate is used in the process.

When an acid addition salt of hydrazine is employed a base such as a trialkylamine (for example triethylamine) is optionally present.

A particularly preferred compound of formula (III) is 1,3,5-trichlorobenzene.

The reaction may be conducted in a solvent chosen from cyclic and aliphatic ethers such as tetrahydrofuran, 1,4-dioxan or 1,2-dimethoxyethane; N-methylpyrrolidone; dimethyl sulphoxide; N,N-dimethylformamide; sulpholane; N,N,N',N'-tetramethylurea; aromatic hydrocarbons which may be substituted with one or more alkyl groups or chlorine atoms, such as chlorobenzene or xylene; and pyridine. Preferred solvents include pyridine, tetrahydrofuran, N,N, N',N'-tetramethylurea and 1,4-dioxan (pyridine and tetrahydrofuran are especially preferred). The amount of solvent used is generally from 1 to 10 ml (preferably from 4 to 8 ml) per gramme of compound of formula (III).

The process is generally performed in an autoclave or other sealed vessel.

The reaction temperature is generally from 50° C. to 250° C., preferably from 120° C. to 200° C. The reaction is generally conducted using from 1 to 20 molar equivalents (preferably 4 to 8 molar equivalents) of the hydrazine source.

A catalyst may optionally be used to increase the rate of the reaction, and when present is generally chosen from alkali and alkaline earth metal fluorides such as potassium fluoride. The amount of catalyst employed is generally from 0.05 to 2 molar equivalents (preferably from 0.5 to 1 molar equivalents). The reaction may also be effected in the presence of copper or a copper salt, preferably copper (I) chloride.

The process of the invention for the preparation of substituted phenylhydrazines of formula (II) and their acid addition salts represents in certain aspects an improvement over the prior art. Process (B) is particularly useful for the preparation of the valuable intermediate 3,5-dichlorophenylhydrazine from 1,3,5-trichlorobenzene, because the reaction proceeds in high yield and isomer purity and provides together with the other processes of the present invention an efficient method for obtaining synthetically valuable intermediate compounds.

Moreover when process (B) is used for the preparation of 3,5-dichlorophenylhydrazine from 1,3,5-trichlorobenzene, the reaction proceeds with excellent regioselectivity.

According to a further feature of the invention processes (A) and (B) can be combined to prepare a substituted aniline of formula (1) or an acid addition salt thereof from a compound of formula (III).

The following non-limiting examples illustrate the invention. Each product was shown to be identical to a known reference sample of the compound.

EXAMPLE 1

Preparation of 3,5-Dichloroaniline from 3,5-Dichlorophenylhydrazine

Raney nickel (2 g of a slurry in water) was added to a solution of 3,5-dichlorophenylhydrazine (1 g) in methanol (5 ml) and heated at 60° C. for 2 hours. The cooled mixture was filtered and evaporated to give the title compound in 100% yield.

EXAMPLE 2

Preparation 3,5-Dichloroaniline from 3,5-Dichlorophenylhydrazine

The procedure of Example 1 was repeated but using two equivalents of Raney nickel and heating at 60° C. for 3 hours in methanol to give the title compound in >90% yield.

EXAMPLE 3

Preparation of 3,5-Dichlorophenylhydrazine

A mixture of 1,3,5-trichlorobenzene (2.53 g), hydrazine hydrate (3.48 g, 5 molar equivalents) and pyridine (12 ml) was heated in an autoclave (purged with argon) for 6 hours at 180° C. The mixture was cooled, the excess hydrazine decanted and the organic phase evaporated in vacuo to give the title compound in 60% yield. It was shown that 65% of the starting material had been consumed, thus indicating that the reaction had occurred with high selectivity.

EXAMPLE 4

Preparation of 3,5-Dichlorophenylhydrazine

The procedure of Example 3 was repeated but using 6 equivalents of hydrazine hydrate gave the title compound in 63% yield. It was shown that 77% of the starting material had been consumed, thus indicating that the reaction had occurred with good selectivity.

EXAMPLE 5

Preparation of 3,5-Dichlorophenylhydrazine

The procedure of Example 3 was repeated but using 6 equivalents of hydrazine hydrate to give after 10 hours at 180° C., the title compound in 76% yield. It was shown that 77% of the starting material had been consumed, thus indicating that the reaction had occurred with high selectivity.

EXAMPLE 6

Preparation of 3,5-Dichlorophenylhydrazine

The procedure of Example 3 was repeated but using 6 equivalents of hydrazine hydrate to give after 6 hours at 200° C., the title compound in 82% yield. It was shown that 83% of the starting material had been consumed, thus indicating that the reaction had occurred with high selectivity.

What is claimed is:

1. A process for the preparation of a substituted aniline of formula (I):

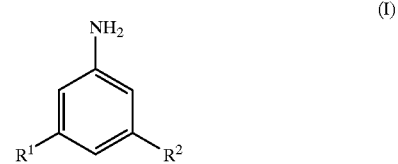

wherein $R^1$ and $R^2$ each independently represent a halogen atom; or an acid addition salt thereof; which process comprises the hydrogenolysis of a substituted phenylhydrazine of formula (II):

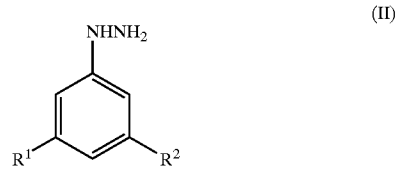

wherein $R^1$ and $R^2$ are as defined above, or an acid addition salt thereof, in the presence of a metal or metal compound under reducing conditions.

2. A process according to claim 1 in which the hydrogenolysis is performed using Raney nickel.

3. A process for the preparation of a substituted phenylhydrazine of formula (II) as defined in claim 1 or an acid addition salt thereof, which comprises the reaction of a compound of formula (III):

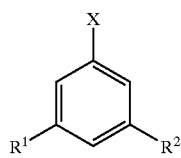

(III)

wherein $R^1$ and $R^2$ are as defined in claim 1 and X represents a halogen atom, with hydrazine or an acid addition salt or source thereof.

4. A process according to claim 3 in which hydrazine hydrate is used.

5. A process according to claim 1 or 2 in which the compound of formula (II) is prepared by a process according to claim 3 or 4.

6. A process according to any one of the preceding claims wherein $R^1$ and $R^2$ represent chlorine.

7. A process according to claims 1, 2, 5 or 6 which further comprises converting the substituted aniline of formula (I) or an acid addition salt thereof into an agriculturally fungicidal compound.

* * * * *